US010377765B2

(12) United States Patent
Jaffe et al.

(10) Patent No.: US 10,377,765 B2
(45) Date of Patent: Aug. 13, 2019

(54) POLYESTER ETHERS DERIVED FROM ASYMMETRICAL MONOMERS BASED UPON BISANHYDROHEXITOLS

(71) Applicant: New Jersey Institute of Technology, University Heights, NJ (US)

(72) Inventors: Michael Jaffe, Maplewood, NJ (US); Willis Hammond, Chatham, NJ (US); Xianhong Feng, Kearny, NJ (US); Anthony East, Madison, NJ (US)

(73) Assignee: New Jersey Institute of Technology, Newak, NJ (US)

(*) Notice: Subject to any disclaimer, the term of this patent is extended or adjusted under 35 U.S.C. 154(b) by 0 days.

(21) Appl. No.: 15/234,606

(22) Filed: Aug. 11, 2016

(65) Prior Publication Data
US 2016/0369046 A1 Dec. 22, 2016

Related U.S. Application Data

(62) Division of application No. 13/050,684, filed on Mar. 17, 2011, now Pat. No. 9,447,230.

(60) Provisional application No. 61/315,227, filed on Mar. 18, 2010.

(51) Int. Cl.
C07D 493/04 (2006.01)
C07D 519/00 (2006.01)
C08G 63/66 (2006.01)
C08G 63/664 (2006.01)
C08G 63/672 (2006.01)

(52) U.S. Cl.
CPC ......... C07D 493/04 (2013.01); C07D 519/00 (2013.01); C08G 63/66 (2013.01); C08G 63/664 (2013.01); C08G 63/672 (2013.01); Y02P 20/55 (2015.11)

(58) Field of Classification Search
CPC .... C07D 493/04; C07D 519/00; C08G 63/66; C08G 63/664; C08G 63/672; Y02P 20/55
See application file for complete search history.

(56) References Cited

U.S. PATENT DOCUMENTS

| 4,297,286 A | 10/1981 | Sandrock et al. |
| 4,435,586 A | 3/1984 | Kruse et al. |
| 4,769,379 A | 9/1988 | Leitold et al. |
| 6,169,124 B1 | 1/2001 | Horn et al. |
| 6,737,481 B1* | 5/2004 | Kurian ............... C08G 63/672 524/483 |
| 2003/0232959 A1 | 12/2003 | Adelman et al. |
| 2007/0282042 A1 | 12/2007 | East |
| 2008/0021209 A1 | 1/2008 | East et al. |
| 2008/0212009 A1 | 9/2008 | Nakano |

FOREIGN PATENT DOCUMENTS

| CN | 101648958 A | 2/2010 |
| JP | 200364170 | 3/2003 |
| JP | 2005530000 | 10/2005 |
| JP | 2010503736 | 2/2010 |
| KR | 20050089743 | 9/2005 |
| WO | 2009146202 | 12/2009 |

OTHER PUBLICATIONS

Chatti et al." Synthesis of New polyethers derived from Isodide under phase-transfer catalysis . . . " J. Appl.Polym. Sci, V.90, 2003, pp. 1255-1266.*
Joachim Tlliem et al "Synthesis of Polyterephthalates Derived from Dianhydrohexitols" Polymer Butletin 11, 365-369 (1984).*
Chatti et al., "Synthesis and properties of new poly(ether-ester)s containing aliphatic diol based on isosorbide. Effects of the microwave-assisted polycondensation", "European Polymer Journal", Oct. 1, 2005, pp. 410-424, vol. 42, No. 2.

* cited by examiner

Primary Examiner — Ling Siu Choi
Assistant Examiner — Gennadiy Mesh
(74) Attorney, Agent, or Firm — Davis, Brown, Koehn, Shors & Roberts, P.C.; Matthew W. Coryell

(57) ABSTRACT

An AB monomer, useful for the production of condensation polymers, wherein the AB monomer has the structure: A-X-C-Y-B; wherein A is reactive carbonyl derivative of carboxylic acids; Y is a bisanhydrohexitol unit derived from the group consisting of isosorbide, isoidide and isomannide; X is selected from the group consisting of: aromatic rings, including 1,4-phenylene, 1,3-phenylene, 2,6-naphthalene 2,7-naphthalene, and substituted derivatives thereof; heterocycles including, 2,5-furan, 2,5-thiophene, substituted 2,5-furan and substituted 2,5-thiophene; and saturated or unsaturated aliphatic chains; B is OH; and C is selected from the group consisting of ether oxygen, a sulfide, and an amine, wherein the amine is NH or NR wherein R is C1 to C6, attaching X to Y.

12 Claims, 8 Drawing Sheets

POLYESTER ETHERS DERIVED FROM ASYMMETRICAL MONOMERS BASED UPON BISANHYDROHEXITOLS

CROSS-REFERENCE TO RELATED APPLICATION(S)

This application is a divisional application of U.S. patent application Ser. No. 13/050,684, filed Mar. 17, 2011, which claims priority to U.S. Patent Application Ser. No. 61/315,227, filed Mar. 18, 2010, each of which are incorporated herein by this reference in their entirety.

BACKGROUND OF THE INVENTION

The present invention relates generally to asymmetrically substituted compounds and, more specifically, to asymmetrically substituted derivatives of bisanhydrohexitols, including isosorbide and isoidide.

Isosorbide is a stable, rigid, dihydroxyether derived from glucose by reduction to sorbitol and acid-catalyzed cyclodehydration. It belongs to a class of compounds called bisanhydro-hexitols, other members being isomannide (from mannose) and isoidide (from idose). Such materials are water soluble and harmless and find widespread use in pharmaceuticals and food chemistry. By far the most widely available is isosorbide, which can be obtained from biomass sources via enzyme hydrolysis to make simple hexose sugars and subsequent hydrogenation to make sugar alcohols. Isosorbide is increasingly becoming used as an intermediate and raw material for polymers, additives and stabilizers.

One of the great advantages of isosorbide, unlike its isomers, is that it has two hydroxyl groups with different topographies and chemical reactivity. One —OH is exo and one is endo and as a result they can be selectively esterified and etherified by use of specific chemical reactions under the correct conditions. This invention discloses a range of products and additives in which this idea is exploited to make multifunctional additives, stabilizers, etc., all based on isosorbide. Incorporation of isosorbide into PET has been shown to raise the Tg of the resulting co-polymer affording a copolymer that has potential as a hot fill bottle resin. However, incorporation of isosorbide into PET on a commercial scale has encountered several problems. The secondary hydroxyl groups of isosorbide make it less reactive than the primary hydroxyls of ethylene glycol. This fact coupled with the volatility of isosorbide make it difficult to get high incorporation into PEIT copolymers and leads to complications with the recycle of the ethylene glycol/isosorbide stream generated during polymerization. It is believed that the different reactivities of the two hydroxyl groups of isosorbide also complicate its polymerization chemistry.

SUMMARY OF THE INVENTION

We have synthesized various AB monomers from isosorbide including an isoidide carbomethoxyphenyl ether (1). In addition, we have synthesized the homopolymer 2 from these AB monomers which represent a new class of polymers.

The present invention consists of novel asymmetrically substituted compounds that are ether derivatives of bisanhydrohexitols. The compounds have applicability as asymmetric or so-called AB, monomers in polymerization reactions. Isosorbide is the preferred starting material as it has one exo and one endo hydroxyl function. The process for making the compounds of the present invention involve a nucleophilic displacement at the 5-position of the isosorbide. The hydroxyl function is acylated with a good leaving group such as p-toluenesulfonyl, benzenesulfonyl or methanesulfonyl to form a reactive ester. This may be nucleophilicly displaced in high yield in a Williamson reaction with an alkali metal phenoxide, such as the potassium phenoxide of methyl 4-hydroxybenzoate. This reaction at the 5-position results in a Walden inversion to give the isoidide ether. Owing to the stereochemistry of isosorbide, only the 5-OH is open to such a reaction. The 2-position may be protected by a removable protective group or kinetic control alone of the acylation employed to give the desired result.

An object of the present invention is to provide novel asymmetrically substituted bisanhydrohexitols.

Another object of the present invention is to provide novel AB monomers comprising asymmetrically substituted bisanhydrohexitols that can be polymerized through a novel self-polymerization reaction to provide homopolymers.

A further object of the present invention is the addition of the novel monomers and or homopolymers to condensation polymers to produce condensation polymers having novel and improved characteristics.

Yet another object of the present invention is to introduce a bisanhydrohexitol moiety into polyester with reduced loss of the bisanhydrohexitol during polymerization.

These and other objects of the present invention will be made apparent to those skilled in the art upon a review and understanding of this specification, including the figures, and the appended claims.

DESCRIPTION OF THE INVENTION

A. Preparation of AB Monomers

Figure 1:
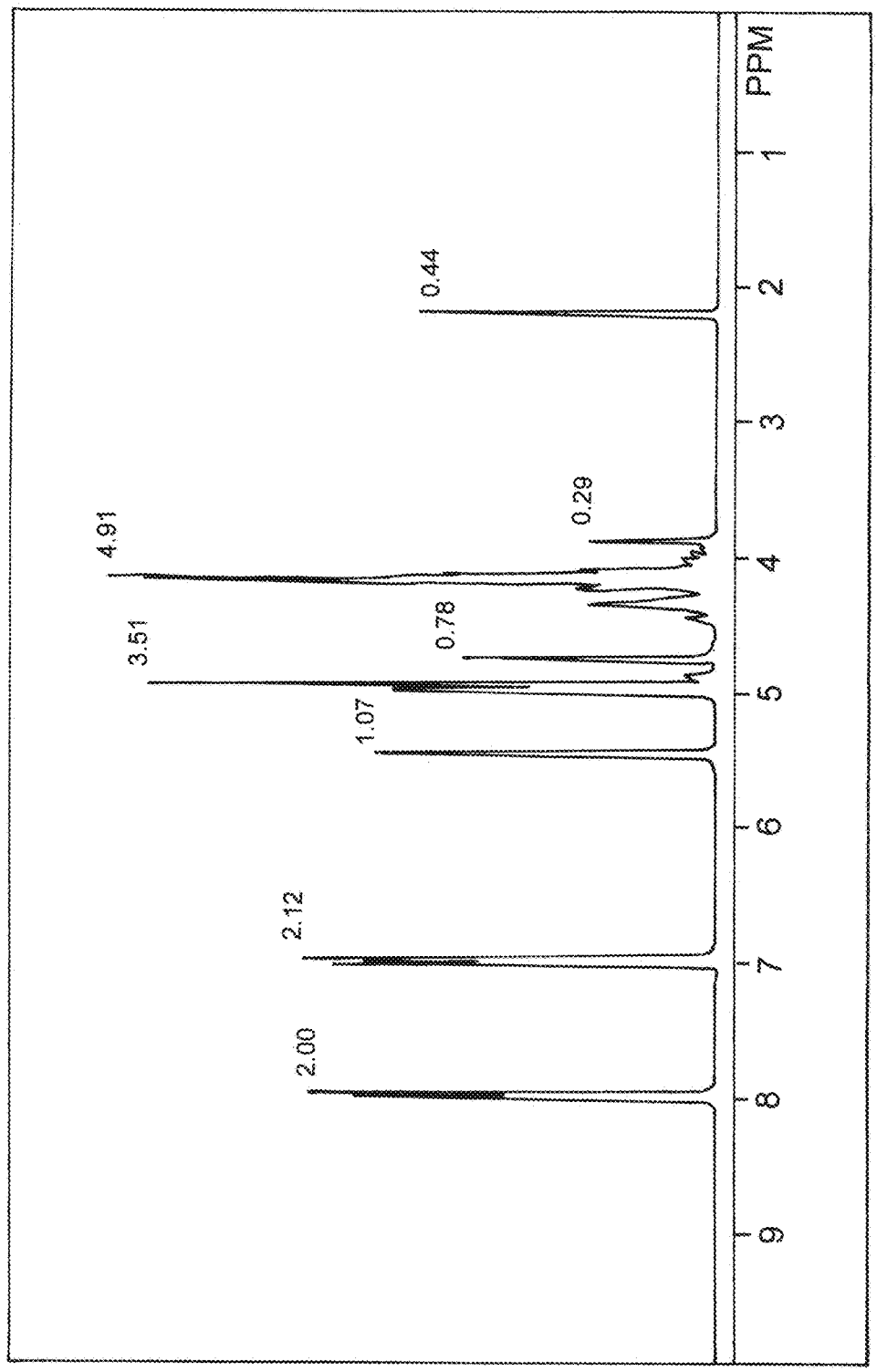
FIG. 1 the 300 MHz 1H NMR spectrum (in TFA-d) of polymer 2.

1. Preparation of 2-Benzyloxy Isoidide 5-(4-carbomethoxy)phenyl Ether (4) from Tosylate (3a)

The reaction was run in a 1000 ml four-neck flask fitted with a sealed Teflon paddle stirrer, reflux air condenser, with a Drierite guard tube, long stem thermometer with a Therm-o-Watch™ sensor while the last neck was fitted with rubber septum. The glassware was dried at 110° C. The flask was charged with 32.6 g (0.088 mole) of isosorbide 2-benzyl ether 5-tosylate (3a), 14 g anhydrous potassium carbonate, 15.0 g (0.097 mole) methyl 4-hydroxybenzoate and 1.0 g of 18-crown-6 ether. The flask was sparged with dry nitrogen through a hypodermic needle inserted in the septum and 300 ml dry dimethylformamide, stored over molecular sieves, added via an 18 gauge double-ended cannula under nitrogen pressure. The solids quickly dissolved at room temperature and the mixture heated to control at 140° C., just below the boiling point of DMF. The mixture was kept under nitrogen. Heating and stirring continued for 18 hrs.

Initially a pale straw color, the reaction mixture was wine colored at the end. After cooling, the mixture was added to 2 liters distilled water and stirred thirty minutes. A thick emulsion formed but eventually this crystallized. The solid was filtered with suction on a 15 cm Buchner funnel and the solid washed repeatedly with water until no odor of DMF was detectable. The product was dried to constant weight in a vacuum oven at 40° C., and after a considerable amount of water had been removed, weighed 22.0 g, (67% theory). The product was recrystallized from 100 ml methanol and after standing at 0° C., deposited glittering platelets. These were dried in the vacuum oven and weighed 19.0 g (59% theory). The product melted sharply at 68-9° C. The proton NMR spectrum was consistent with the desired structure.

2. Preparation of Mesylate 2-benzyloxyisosorbide Ester (3b)

In a dry 5000 ml 4-neck flask fitted with a paddle stirrer, nitrogen inlet fitted to a pressure-equalizing 250 ml tap-funnel, a long stem alcohol thermometer and an air condenser fitted with a nitrogen outlet via a bubbler tube, were placed 1000 ml dry pyridine and 252.0 g (1.07 mole) of recrystallized isosorbide 2-benzyl ether, mp 99-100° C. The mixture was sparged with nitrogen and stirred until all the solid dissolved. The flask was mounted in a large bath full of ice-salt mixture and chilled to 0-5° C. Methanesulfonyl chloride, 97 ml, 134 g. (1.17 mole) was added dropwise (1 drop every 2 seconds) with steady stirring, keeping the reaction mixture around 0-2° C. and never above 5° C. The addition took about six hours. The flask was stoppered and placed in a freezer chest at −15° C. overnight.

Next day the mixture was allowed to warm up to about 5° C. and the tap funnel, thermometer and stirrer refitted with the nitrogen inlet and outlet. Distilled water (100 ml) was added dropwise until the cloudiness due to pyridinium chloride had disappeared. The contents of the flask were then added to a well-stirred 10-lite beaker containing 6000 ml deionized water and 2 kilos of crushed ice. After ten minutes of stirring, the product began to crystallize out. The mixture was stirred for 30-40 minutes, and the product was filtered off with a 24 cm Buchner funnel using a 15-liter filter bottle. The solid was washed with dilute hydrochloric acid (1N), until the solid no longer smelled of pyridine, then washed again with water until the washings were neutral. The solid was sucked dry under a large glass lid and then dried overnight at 30 inches of Hg in a vacuum oven at 50° C. The final yield of white solid was 307.7 g. 91.6% theoretical, mp 91-2° C. TLC on silica showed one spot only, Rf 0.59 in a 3/1 v/v chloroform/acetone mobile phase. The crude product was pure enough for the next reaction stage, but a 25 g. portion was recrystallized from boiling methyl t-butyl ether to give small, glittering needles, mp 92-3° C.

3. Preparation of 2-Benzyloxy Isoidide 5-(4-carbomethoxyphenyl) Ether (5) from Mesylate (3b)

A 500 ml 4-neck flask was fitted with a sealed paddle stirrer, a nitrogen inlet and outlet and a long stem thermometer. All glassware was dried at 110° C. in the oven. The flask was charged in order with 300 ml dry DMF, 31.4 g (0.10 mole) isosorbide-2-benzylether-5-mesylate (3b), 16.7 g (0.11 moles) methyl 4-hydroxybenzoate, 20 g anhydrous potassium carbonate and 1.5 g 18-crown-6 ether. The system was sparged with dry nitrogen and a Therm-o-Watch detector fitted to the thermometer so as control the batch to 135° C., i.e. below the boiling point of DMF. The mixture was stirred and heated for 24 hrs at this temperature. In the early stages, the reaction mixture became very stiff and had to be stirred manually to break up a thick mass but subsequently mechanical stirring was trouble-free. Next day the mixture was an opaque grey suspension. It was left to stir at room temperature for 24 hours then added to 1 liter of distilled water in a 2-liter beaker with vigorous stirring A milky emulsion formed, but soon solid began to deposit on the walls of the beaker and the liquid slowly cleared. After stirring for another 30 minutes, the crystalline solid was scraped off and the suspension of liquid and crystals filtered on a 7 cm Buchner funnel using a #4 filter paper. The off-white solid was washed repeatedly with water and sucked dry on the filter. The damp-dried product weighed 37 g and, after drying at 45° C. in a vacuum oven, weighed 32.5 g (88% theory).

The crude product was recrystallized from 160 ml methanol and gave a white crystalline solid weighing 24.6 g (66% theory), mp 68-70° C. A second recrystallization raised this to 69-70° C., identical with the material prepared from the tosylate.

4. Reduction of 5-(4-carbomethoxybenzoxy)-2-benzyloxy-Isoidide (5) to Isoidide 2-(4-carbomethoxyphenyl) Ether (1)

To a LabCrest pressure bottle containing 200 ml methanol and 0.94 g of pre-reduced 10% Pd/carbon catalyst was added 18.5 g (0.05 mol) of 5-(4-carbomethoxyphenoxy)-2-benzyloxy-isoidide. After several cycles of 75 psi N2 followed by evacuation to <0.5 mm Hg, the manifold was pressurized to 75 psi with hydrogen and stirring was begun. Over a period of 18 hrs, the pressure dropped 23 psi (theoretical. 26 psi). The system was vented, and the methanol solution of product was filtered to remove catalyst. The methanol was removed on a Rotavap to yield 15.6 g of a clear oil which solidified on standing. The product was recrystallized from 100 ml of methanol to give 10.4 g (72% yield) of white crystals, mp 117-118° C. The crystals were one spot pure by TLC (CHCl3:acetone 3:1). 1H NMR (H1714, CDCl3/TMS): 8.00 (2H, d. 8 Hz), 6.96 (2H, d. 8 Hz), 4.84 (1H, m.), 4.78 (1H, d.), 4.63 (1H, d.), 4.40 (1H, br.), 4.06 (2H, ab q.), 3.94 (2H, ab q.), 3.89 (3H, s.) 2.1 (1H, b.). The reactions are illustrated in Scheme 1.

Scheme 1: Isoidide 2-(4-carbomethoxyphenyl) ether (1)

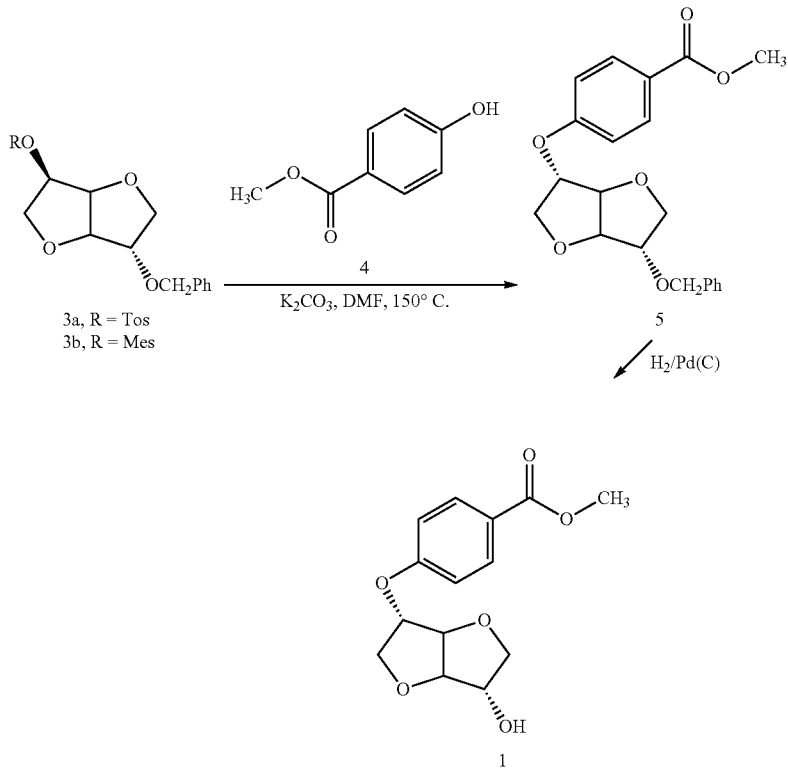

B. Preparation of Polymers from the Monomers

1. First Polymerization of Isoidide 2-(4-Carbomethoxyphenyl) Ether (1) to Make Polymer 2

The polymerization was run in the melt in a glass mini-polymerization reactor apparatus designed to take 10-20 grams of monomer. It was stirred with a sealed Herschberg nichrome wire stirrer and immersed in a tall oil-bath heated and controlled by a digital power unit. The polymerizer was connected directly to a high vacuum trap and a vacuum pump capable of achieving 0.01 mm Hg. All the melt polymerizations described below were run in very much the same way.

The cold apparatus was charged with 10.0 g of isoidide 2-(4 carbomethoxy)phenyl ether (mpt 116-17° C.) and exhausted to 0.01 mm Hg to dry out the apparatus and monomer and remove all traces of moisture and other volatiles. Next the vacuum was released with dry nitrogen and the catalyst added, a solution of 5.0 ml of (liquid) titanium tetra-isopropoxide (TIPT) dissolved in 1.0 ml of dichloromethane added form a micro-syringe through a septum in the side arm. The vacuum was re-applied to evaporate the solvent and heating commenced. The oil bath was heated to 160° C. over one hour and when the monomer was molten, agitation commenced. The bath was held at 160° C. for three hours. The melt, initially clear, began to bubble briskly and eventually went opaque and white. It also grew more viscous and the bubbling ceased. The oil bath was held at 165° C. for one hour then raised slowly in 10° C. steps to 277° C. The vacuum was 0.05 mm Hg. After heating at 277° C. the melt was maintained at this temperature for thirty minutes. Then the oil bath was removed and the system allowed to cool without agitation and eventually the vacuum was let down with dry nitrogen to atmospheric pressure.

Figure 2:
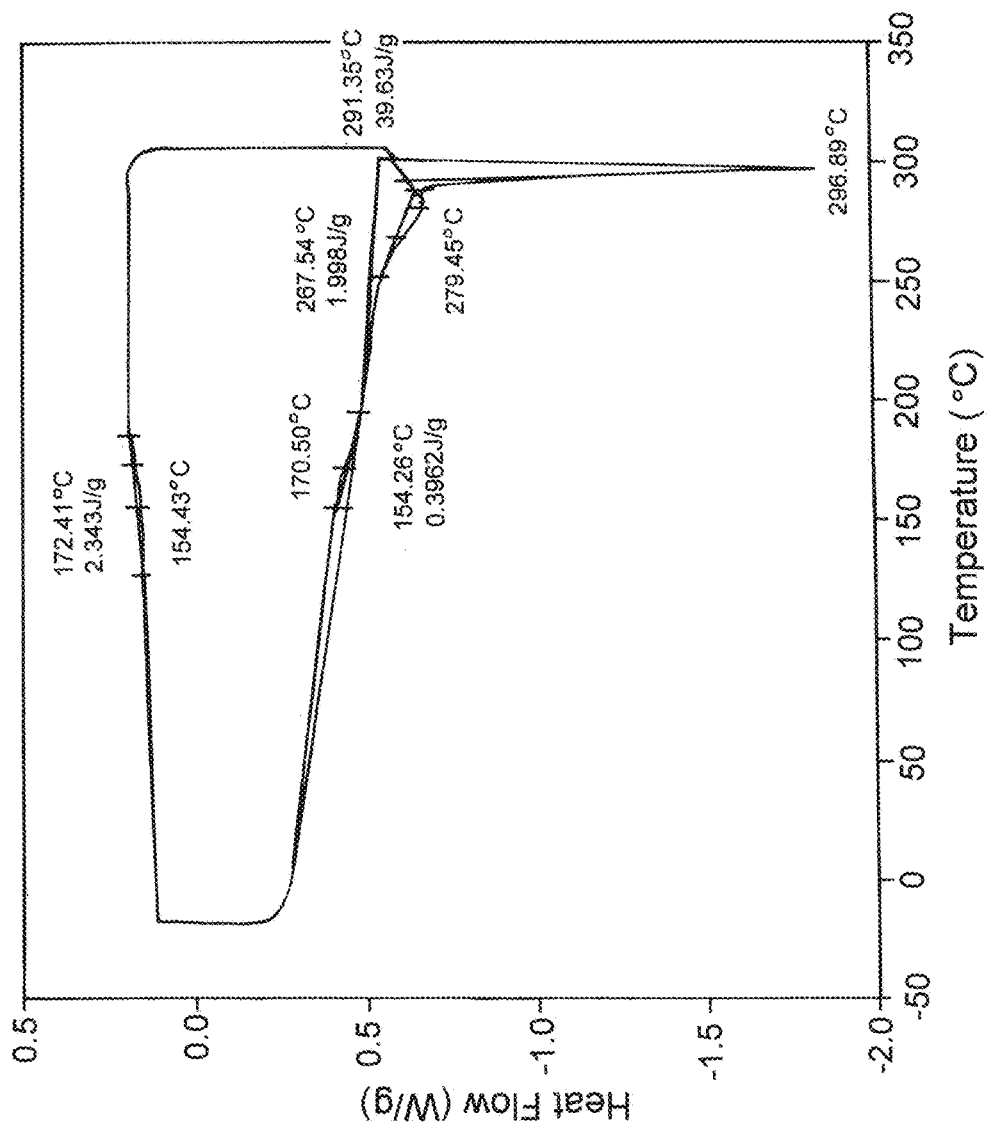
FIG. 2 is a chart of the DSC analysis of polymer 2.
Figure 3:
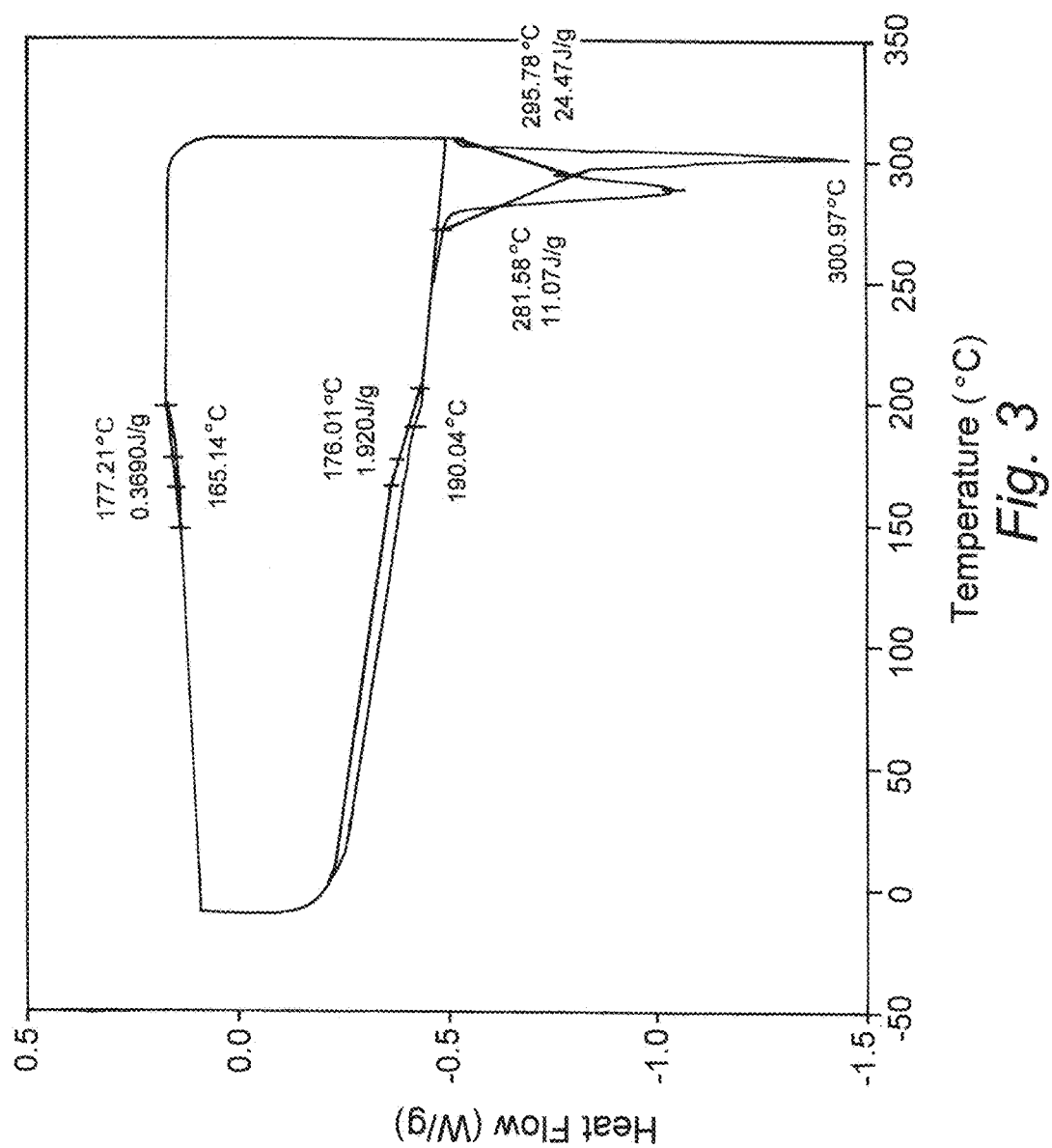
FIG. 3 is a chart of the DSC analysis of polymer 2 after annealing.

The polymer button was removed and broken from around the stirrer. It weighed 4.7 g and was ground into a powder. Some was dissolved in TFA-d and the NMR spectrum) in TFA-d, FIG. 1) showed that it was a low molecular weight polymer with the expected structure and from end-group calculations had a DP of about 20, corresponding to a Mn of ca 5000 g/mole. DSC (FIG. 2) showed a Tg at about 170° C. and a Tm around 300° C. The isolated solid was heated in a tube in the oil bath under nitrogen to anneal it. After four hours at 260° C., the DSC was measured again (FIG. 3) and showed that the Tg had risen slightly to about 176° C. While the Tm was not changed, the degree of crystallinity, as judged by the enthalpy change (peak area), had notably increased. The reactions are illustrated in Scheme 2.

Scheme 2: Polymerization of Isoidide 2-(4-carbomethoxyphenyl) ether (1)

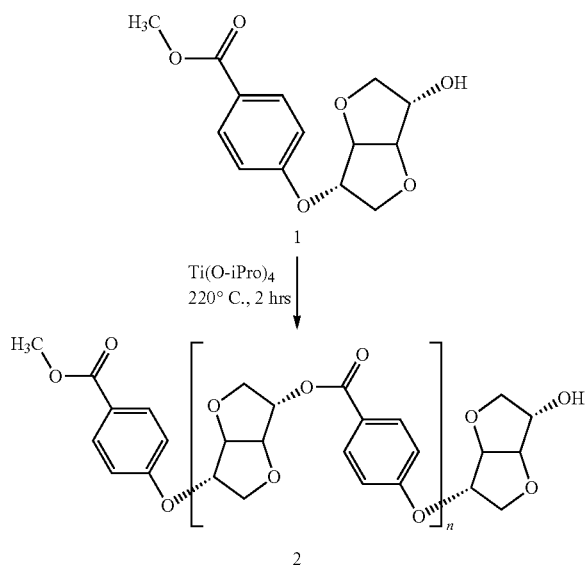

2. Second Polymerization of Isoidide 2-(4-carbomethoxyphenyl) Ether, Isoidide AB-Ether (1)

Figure 4:
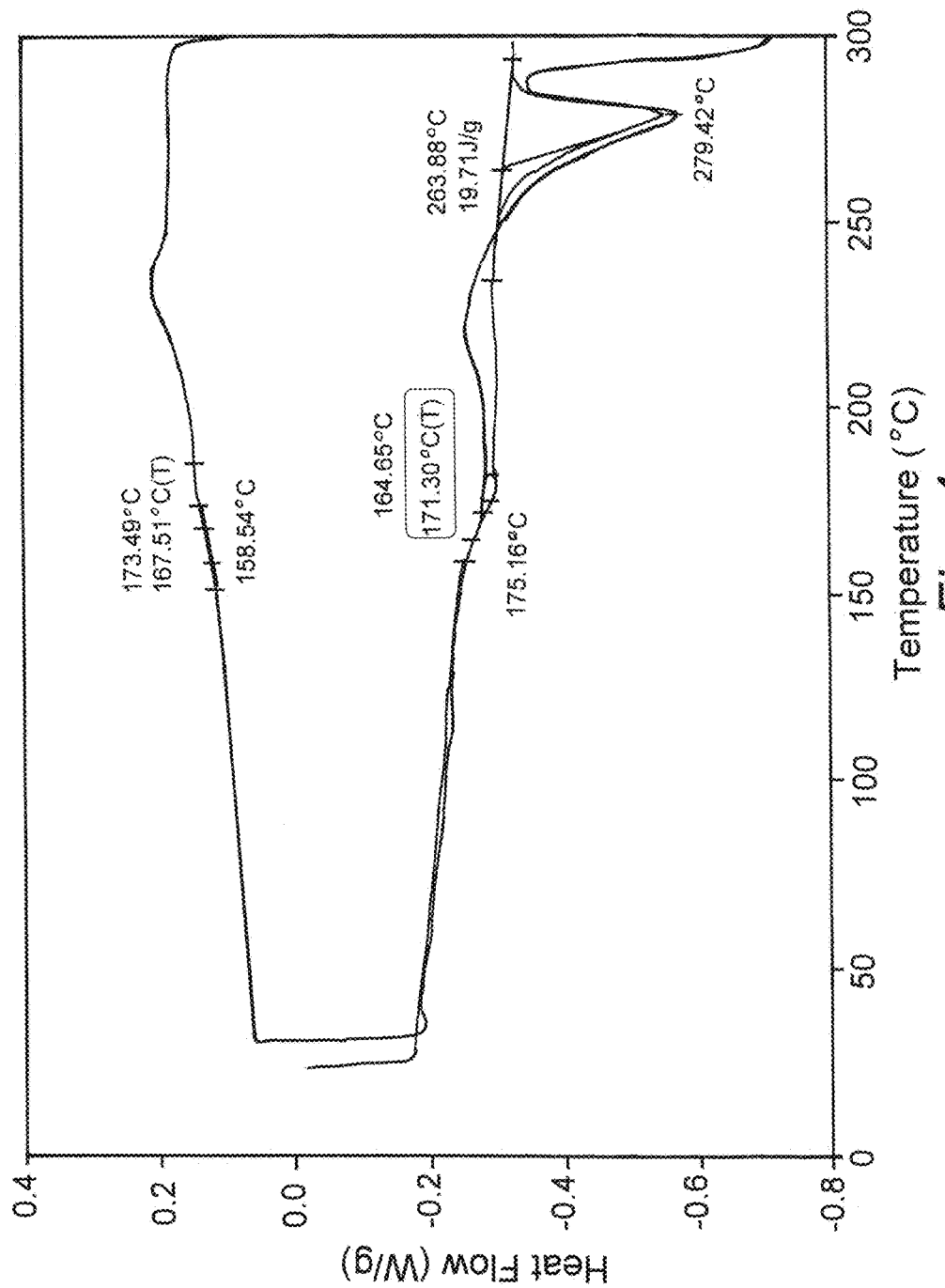
FIG. 4 is chart of the DSC analysis of a first experiment producing polymerized 1.
Figure 5:
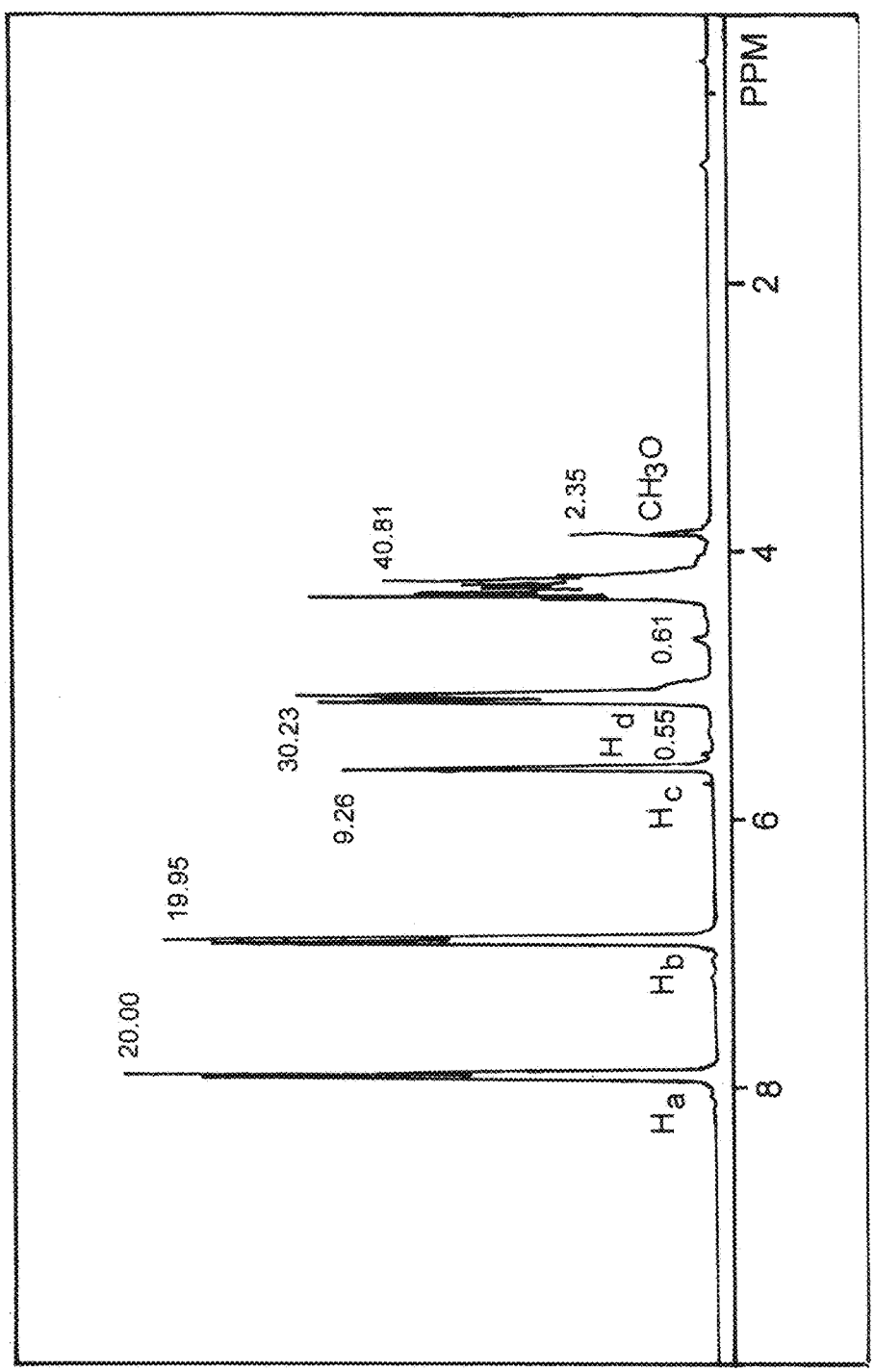
FIG. 5 is the 300 MHz 1H NMR spectrum of the polymer produced in the experiment producing polymerized 1.
Figure 6:
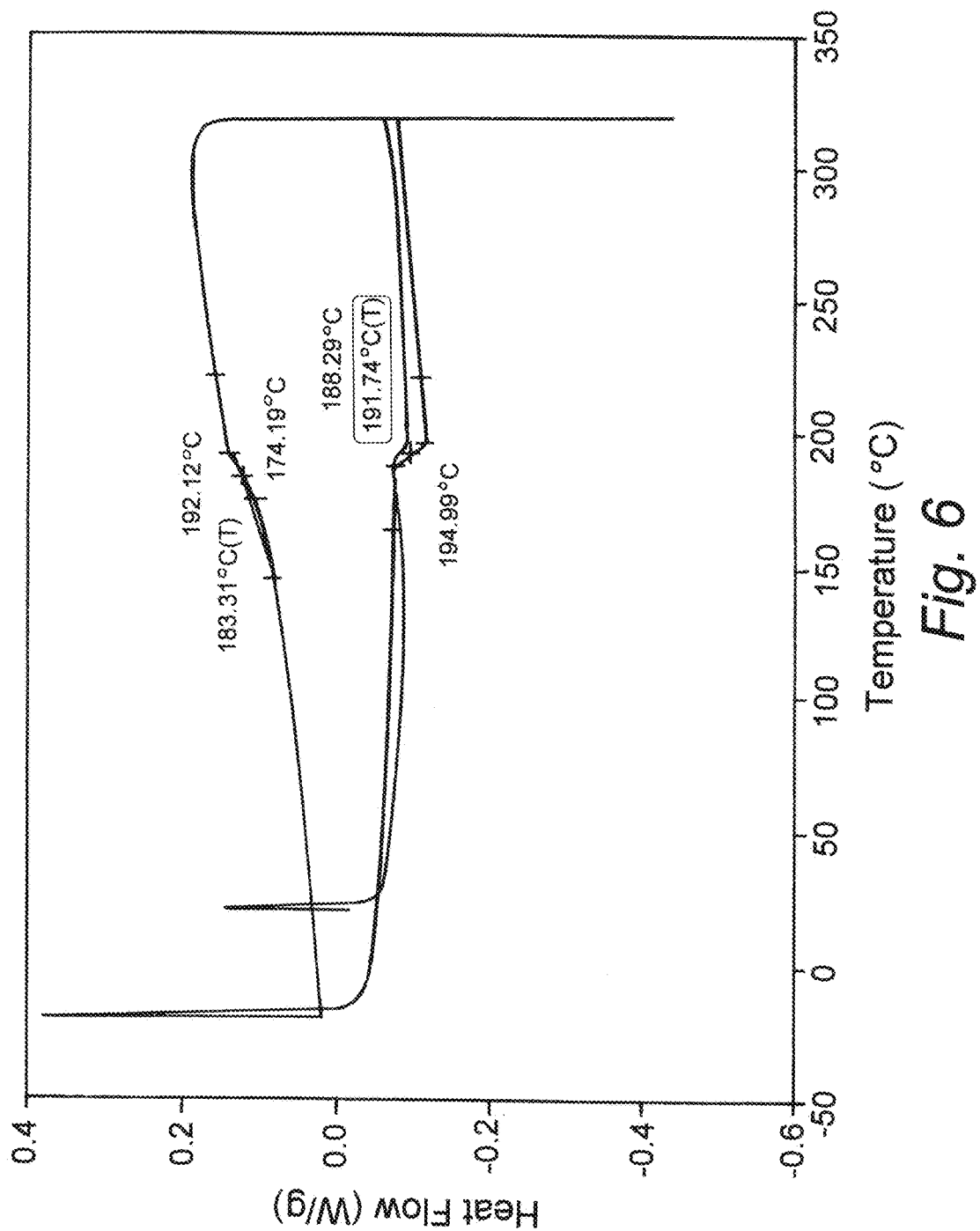
FIG. 6 is chart of the DSC analysis of a second experiment producing polymerized 1.
Figure 7:
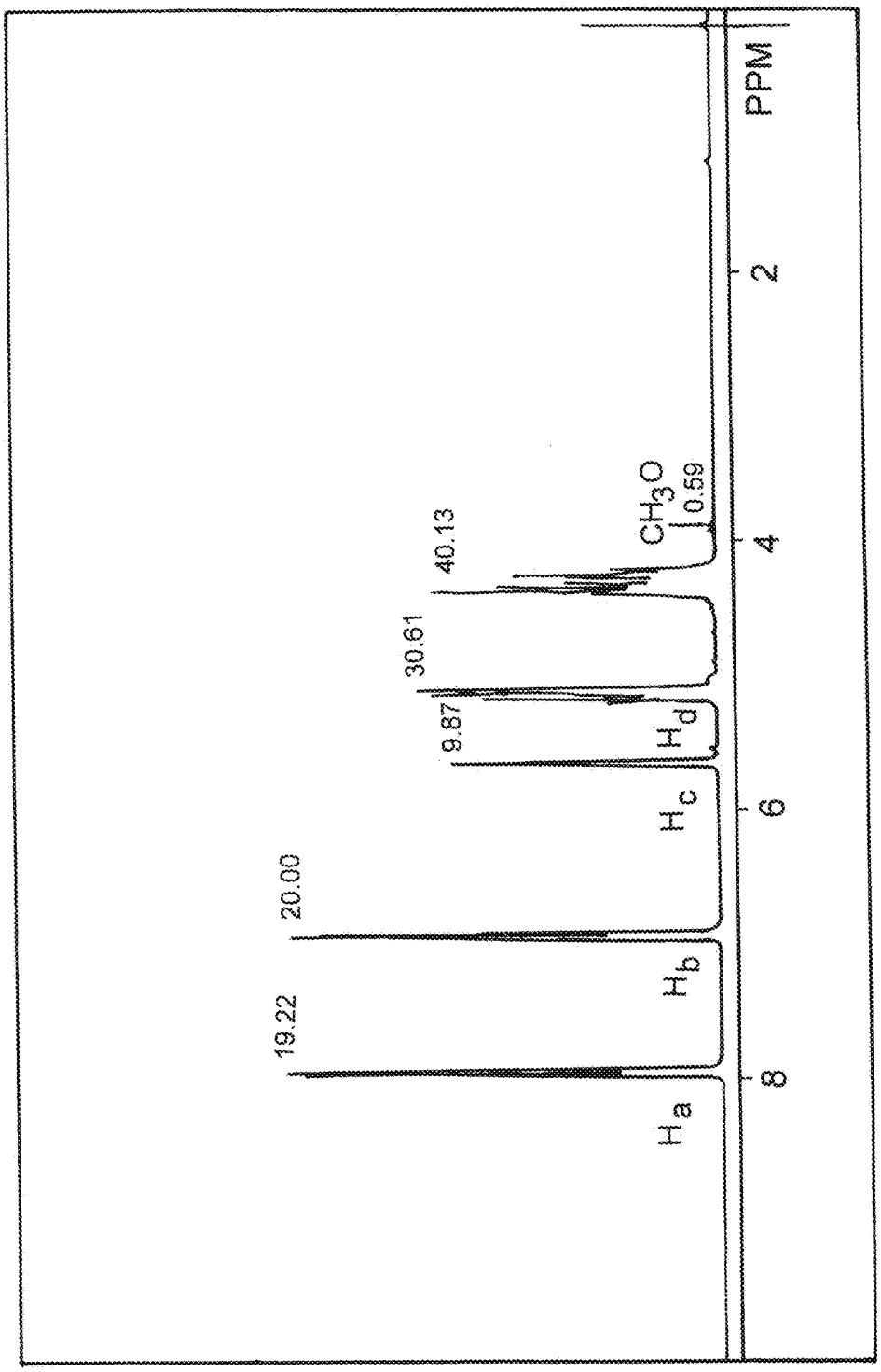
FIG. 7 is the 300 MHz 1H NMR spectrum of the polymer produced in the second experiment producing polymerized 1.

Isosorbide AB-ether 1 (14.16 g, 99% pure by DSC) was placed in micro polymerization reactor as described above and the reactor was evacuated for 1 hr at 100° C./15 mm Hg to dry monomer. The reactor was filled with dry nitrogen and 5.6 µl of pure titanium tetraisopropoxide catalyst (64 ppm Ti) dissolved in 1 ml of dry benzene and 45 mg Irganox 1076 dissolved in 0.75 ml benzene was added. The apparatus was evacuated to 1 mm Hg and filled with dry nitrogen. This was repeated twice more to remove traces of oxygen. The reactor under dry nitrogen at 1 atm. was heated to 150° C. in a temperature controlled fluidized bed heater to melt the monomer. The stirrer was turned on and the reactor was evacuated to 50 mm Hg. The temperature was raised to 200° C. in one step and then in 10° C. increments to 270° C. as the vacuum was reduced in increments to 0.4 mm Hg over a 40 minute period. Over the next 2.5 hours the temperature was gradually raised to 295° C. and held at 295° C. for one-half hour with the vacuum maintained below 0.4 mm Hg. The reactor was filled with dry nitrogen to 1 atm, the stirrer was raised from the molten polymer and the reactor was removed from the fluidized bed heater to cool. On fully cooling, a light brown crystalline solid was removed from the reactor. The solid showed a Tg=171° C. (2nd heat) and two melting points at 279 and 299° C. (FIG. 4). The NMR spectrum (FIG. 5 in TFA-d) was consistent with the desired homopolymer with a DP=12.8 and an Mn=3180 g/mol. A repeat of the experiment ending with a final temperature of 310° C. gave a polymer with a Tg=191° C. and Tm>320° C., a DP=50 (FIG. 6) and Mn=12500 (by NMR, FIG. 7; it is assumed that the peak at 3.8 ppm (CH3O—) in the NMR spectrum represents one end of the homopolymer.). The data from five polymerization reactions are summarized in Table 1 which tabulates the dependence of Mn and Tg on Tmax, the highest temperature that was attained in each polymerization.

TABLE 1

Relation between Tmax, Mn and Tg Poly 1

| expt # | Tmax (° C.) | Mn (g/mol) | Tg (° C.) |
|---|---|---|---|
| 1 | 220 | 1786 | 125 |
| 2 | 240 | 1265 | 136 |
| 3 | 275 | 2200 | 172 |
| 4 | 295 | 3180 | 171 |
| 5 | 310 | 12400 | 191 |

Discussion

Figure 8:
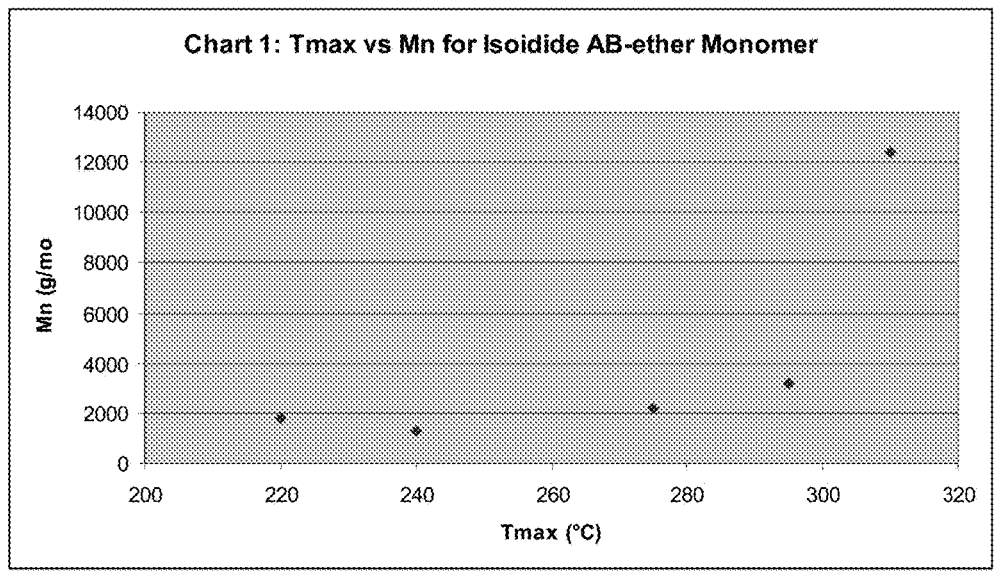
FIG. 8 is a chart of Tmax versus number-average molecular weight for the five experiments producing polymerized 1.
Figure 9:
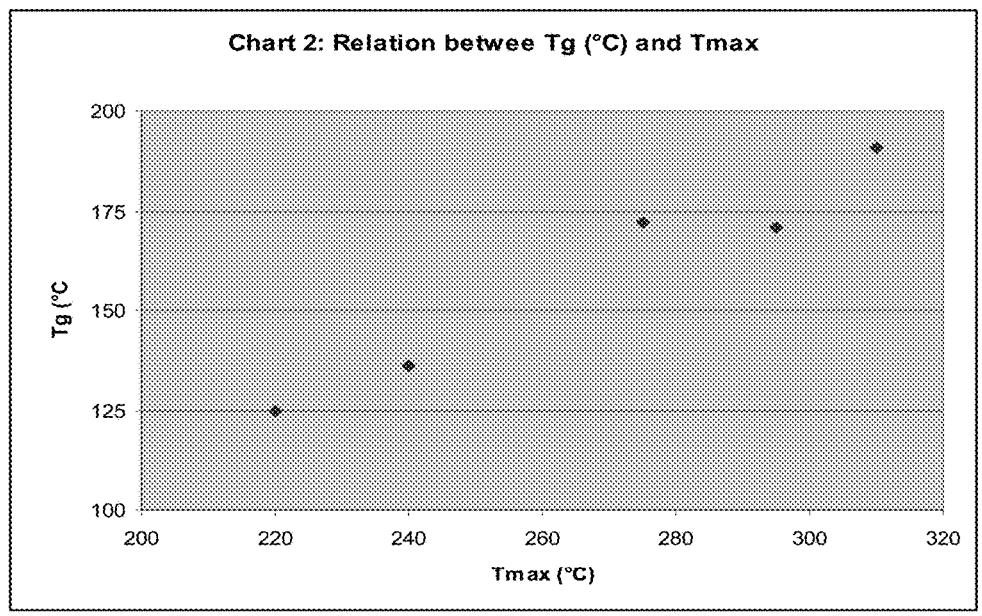
FIG. 9 is a chart of Tg versus Tmax for the five experiments producing polymerized 1.

From Table 1, it appears that the maximum molecular weight obtained for poly(isoidide AB-ether) 1 is determined by the maximum temperature attained in the polymerization. This is shown nicely in FIG. 7 where it is seen that the molecular weight of the polymer goes up significantly with a polymerization temperature>300° C. At 300° C. there is also noticeable decomposition occurring as evidenced by the color of the polymer. A number of variables need to be optimized to obtain the best polymer, e.g. temperature program, time at Tmax, purity of the monomer, alternative catalysts. FIG. 8 shows that Tg increases with Mn. Because of scatter in the data it is not obvious what the limiting Tg might be for the homopolymer.

Results

Using the Sn2 inversion chemistry it was possible to make the isoidide AB-monomer 1 in high yield and purity starting with either the tosylate (3a) or mesylate (3b). This produces an AB monomer with an ether link which is expected to be more stable than an ester link. This monomer leads to another new class of polymers.

The AB monomer 1 was successfully polymerized to give homopolymer 2 with a number average molecular weight, Mn, determined by NMR end group analysis of ca 5,000 g/mol as outlined in scheme 15. This is the first isoidide containing homopolymer of its kind. In addition to being a new polymer it is believed that the homopolymer can be incorporated in PET and PLLA by transesterification to raise the Tg of these polymers. Using the proper catalyst and thermal conditions it may be possible to incorporate 2 into a copolymer as a block. A chemical scheme for implementation of the AB monomer into PET via transesterification can be seen below:

Scheme 3: Incorporation of AB monomer 1 into PET to form novel copolymer.

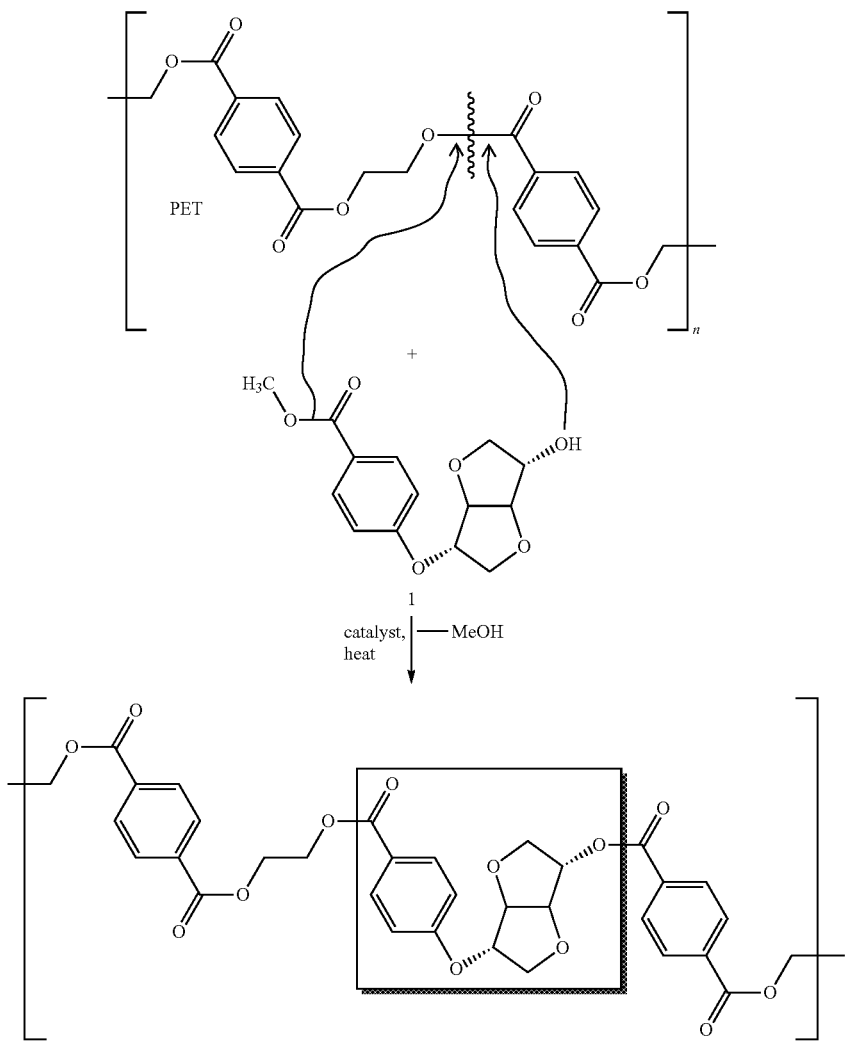

Due to the ether linkage this material will not scramble through transesterification which leads to a unique polymer with a defined structure.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. An AB monomer, comprising bisanhydrohexitol derivatives capable of self-polymerization to form stereoregular or regioregular condensation polymer, wherein the AB monomer has the structure:

A-X-C-Y-B wherein A is a carboxylic acid, an ester, or an acid chloride;

Y is a bisanhydrohexitol unit derived from the group consisting of isosorbide, isoidide and isomannide;

X is selected from the group consisting of:
a. aromatic rings, including 1,4-phenylene, 1,3-phenylene, 2,6-naphthalene 2,7-naphthalene, and substituted derivatives thereof;
b. heterocycles including, 2,5-furan, 2,5-thiophene, substituted 2,5-furan and substituted 2,5-thiophene; and
c. saturated or unsaturated aliphatic chains;

B is —OH; and

C is selected from the group consisting of ether oxygen, a sulfide, and an amine, wherein the amine is NH or NR wherein R is C1 to C6, attaching X to Y; and wherein the AB monomer is at least about 98% pure endo-substituted bisanhydrohexitol derivative or an at least about 98% pure exo-substituted bisanhydrohexitol derivative.

2. The AB monomer of claim 1, wherein X is 1,4-phenylene and C is oxygen.

3. The AB monomer of claim 1, wherein X is 1,3-phenylene and C is oxygen.

4. The AB monomer of claim 1, wherein X is 1,4-cyclohexane and C is oxygen.

5. The AB monomer of claim 1, wherein X is 2,5-furan and C is oxygen.

6. The AB monomer of claim 1, wherein X is a pentamethylene and C is oxygen.

7. The AB monomer of claim 1, wherein X is a trimethylene and C is oxygen.

8. The AB monomer of claim 1, wherein X is 1,4-phenylene and C is NH.

9. The AB monomer of claim 1, wherein X is 1,3-phenylene and C is NH.

10. The AB monomer of claim 1, wherein X is a pentamethylene and C is NH.

11. The AB monomer of claim 1, wherein A is an ester derivative of a carboxylic acid, X is 1,4-phenylene, C is an ether oxygen, Y is isosorbide, and B is —OH.

12. The AB monomer of claim 1, wherein A is an ester derivative of a carboxylic acid, X is 1,4-phenylene, C is an ether oxygen, Y is isoidide, and B is —OH.

* * * * *